United States Patent [19]

Sherlock

[11] Patent Number: 4,492,702

[45] Date of Patent: Jan. 8, 1985

[54] 1-PHENYL-1,8-NAPHTHRIDIN-2(1H)-ONES

[75] Inventor: Margaret H. Sherlock, Bloomfield, N.J.

[73] Assignee: Schering Corporation, Madison, N.J.

[21] Appl. No.: 533,674

[22] Filed: Sep. 19, 1983

Related U.S. Application Data

[63] Continuation-in-part of Ser. No. 438,681, Nov. 3, 1982, abandoned.

[30] Foreign Application Priority Data

Apr. 20, 1983 [EP]  European Pat. Off. ........ 83103839.3

[51] Int. Cl.$^3$ .................. A61K 31/435; C07D 471/04
[52] U.S. Cl. .................................... 424/256; 546/122; 424/250; 424/251; 424/248.58; 544/127; 544/333; 544/362; 544/350

[58] Field of Search .......................... 424/256; 546/122

[56] References Cited

FOREIGN PATENT DOCUMENTS 116495  9/1977  Japan .

*Primary Examiner*—Jane T. Fan
*Attorney, Agent, or Firm*—Stephen I. Miller

[57] ABSTRACT

Certain substituted 1,8-naphthyridines and 1,5,8-azanaphthyridines are useful for treating allergic reactions in mammals. Certain of the compounds may also be utilized to treat chronic obstructive lung diseases in mammals.

Methods for preparing the compounds and methods for their use are also described.

47 Claims, No Drawings

1-PHENYL-1,8-NAPHTHRIDIN-2(1H)-ONES

This application is a continuation-in-part copending U.S. Ser. No. 438,681 filed Nov. 3, 1982 now abandoned.

BACKGROUND OF THE INVENTION

Japanese patent public disclosure (Kokai) No. 116495/77, Sept. 29, 1977 discloses various naphthyridine derivatives which allegedly possess analgesic, antiinflammatory, central nervous system depressant and diuretic effects. There is no indication that the compounds disclosed in Japanese publication have activity against chronic obstructive lung diseases such as asthma, bronchitis and the like or that these compounds would be useful for treating allergic reactions.

SUMMARY OF THE INVENTION

The invention sought to be patented in its first pharmaceutical method aspect is a method for treating allergic reactions in a mammal which method comprises administering an antiallergic effective amount of a compound having the structural formula I

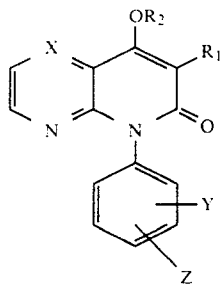

wherein
X is CH or N;
Y is hydrogen, hydroxy, benzyloxy, amino, sylfamyl, halogen, nitro, alkyl having from 1 to 6 carbon atoms, alkoxy having from 1 to 6 carbon atoms, carboxylic acyl having from 2 to 6 carbon atoms, alkyl-S(O)$_m$- having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;
Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;
R$_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, 2-, 3- or 4-pyridyl, 2-, 4-, 5- pyrimidyl, 2- or 3- thionyl, 2- or 3- furanyl, carboxylic acyl having from 2 to 6 carbon atoms, or alkyl having from 1 to 10 carbon atoms which may be substituted with —COOH, hydroxy, halogen, alkoxy having from 1 to 6 carbon atoms, phenyl, 2-, 3- or 4-pyridyl, 2-, 4- or 5-pyrimidyl, 2- or 3- thienyl, 2- or 3-furanyl, carboxylic acyl having from 1 to 6 carbon atoms, cycloalkyl having from 3 to 7 carbon atoms or carboxylic acyloxy having from 1 to 6 carbon atoms;
R$_2$ is hydrogen, alkenyl having from 3 to 8 carbon atoms, alkynyl having from 3 to 8 carbon atoms, carboxylic acyl having from 1 to 6 carbon atoms, R$_a$R$_b$N(CH$_2$)$_n$- (wherein R$_a$ and R$_b$ are hydrogen, alkyl having from 1 to 6 carbon atoms or may be joined to complete a piperidine, morpholine, piperazine or pyrrolidine ring and n is an integer of from 2 to 6 ), hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or amine; with the proviso that when X is CH, Y and Z are both hydrogen and R$_1$ is n-butyl; R$_2$ is not hydrogen or a cation derived from a pharmaceutically acceptable metal or an amine and with the further proviso that when X is CH, Y and Z are both hydrogen, and R$_1$ is n-butyl; R$_2$ is not allyl.

The preferred value for X is CH.

The preferred values for Y are hydrogen, methoxy, trifluoromethyl, methylthio; the more preferred value is hydrogen.

The perferred values for Z are hydrogen and methyl.

The preferred values for R$_1$ are n-alkyl having from 3 to 5 carbon atoms, alkenyl having from 3 to 4 carbon atoms, omega-hydroxyalkyl having 2 to 4 carbon atoms, and omega-carboxylicacyloxyalkyl having from 6 to 9 carbon atoms; the most preferred values are n-butyl, propen-2-yl, 2-hydroxyethyl, 3-hydroxypropyl and 4-propanoyloxybutyl.

The preferred values for R$_2$ are hydrogen, carboxylic acyl of from 2 to 4 carbon atoms, hydroxyalkyl of from 2 to 4 carbon atoms, R$_a$R$_b$N(CH$_2$)$_n$- (wherein R$_a$ and R$_b$ are hydrogen or alkyl having from 1 to 6 carbon atoms and n is an integer from 2 to 6 carbon atoms) and the cations derived from sodium, potassium, calcium, ethanolamine, N-methylglucamine, diethanolamine, ethylenediamine, tris-(hydroxymethyl)aminomethane and lysine; the most preferred values are hydrogen, ethanoyl, propanoyl, 2-hydroxyethyl, and the cations derived from sodium, N-methylglucamine and lysine.

Preferred methods of the invention for treating allergic reaction in a mammal comprise the administration of an antiallergic effective amount of a compound chosen from among those having the formula I$_a$-I$_f$:

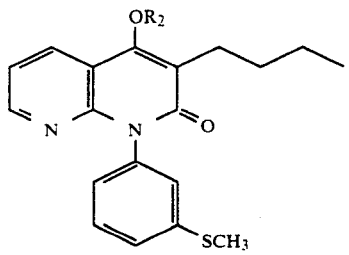

I$_a$

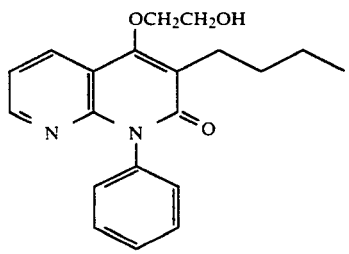

I$_b$

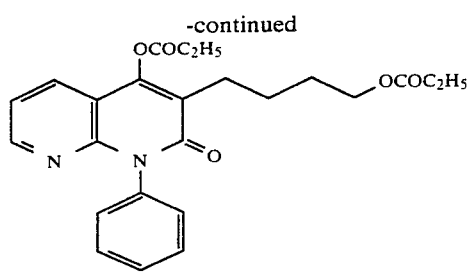

Ic

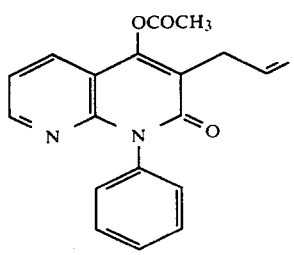

Id

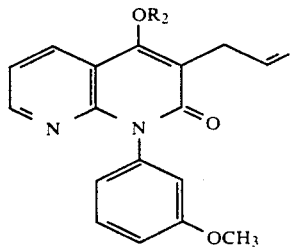

Ie

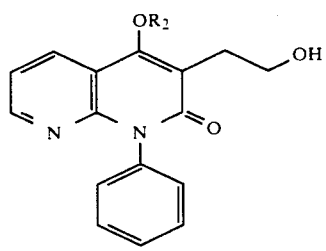

If wherein $R^2$ is hydrogen or the sodium cation.

The invention sought to be patented in its second pharmaceutical method aspect is a method for treating chronic obstructive lung disease in a mammal which method comprises administering an anti-chronic lung disease effective amount of a compound having the structural formula I.

Preferred methods of the invention for treating chronic obstructive lung disease in a mammal comprise the administration of an antichronic lung disease effective amount of a compound chosen from among those having the structural formulae $I_a$–$I_f$.

Certain of the compounds which are utilized in the methods of the invention are disclosed in Japanese patent public disclosure (Kokai) 116495/77, Sept. 29, 1977. The majority of the compounds utilized in the methods herein are novel in view of this publication.

DESCRIPTION OF THE INVENTION

The compounds which are utilized in the methods of the invention may be prepared by methods known to those skilled in the art. For example, a compound having structural formula II

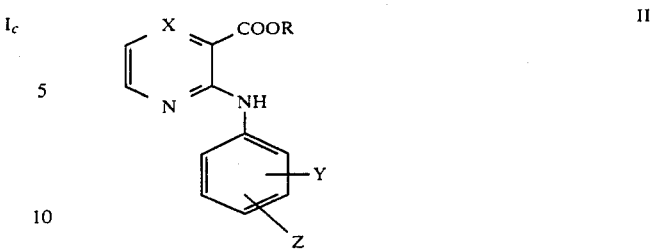

II wherein X, Y and Z are defined hereinabove and R is any convenient alkyl group may be reacted with a compound having structural formula III

$R_1CH_2CO_2R$    III to directly produce the desired compounds wherein $R_2$ is hydrogen. This reaction is preferably accomplished by contacting the two reactants in the presence of a base such as a metal alkoxide e.g. potassium tertiary butoxide or the like, at an elevated temperature e.g. 60° to about 160° C. for a sufficient time until the reaction is substantially completed. The reaction is preferably conducted in an inert atmosphere such as nitrogen. Alternatively, the reaction may be conducted in the presence of a non-reactive solvent such as toluene, xylene etc. The so produced compounds having structural formula I wherein $R_2$ is hydrogen may be converted to compounds having other disclosed values of $R_2$ by standard procedures such as acylation, alkylation and the like.

Certain substituents present in the $R_1$ group may be interconverted by standard procedures, if desired, subsequent to the above described ring closure reaction. For example, a hydroxyl substituent may be converted to a halogen substituent such as a chlorine substituent by treatment with a halogenating agent such as thionyl chloride. Other such interconversions are contemplated herein and will be familiar to those skilled in the art.

The starting materials having structural formulas II and III are known in the art. For example, 2-phenylamino-3-pyridine carboxylic acids (II, X=CH) may be prepared as described in U.S. Re. Pat. No. 26,655. The relevant teachings of this patent are incorporated herein by reference. The requisite 2-phenylamino-3-pyrazine carboxylate esters (II, X=N) may be prepared substantially as described herein starting with a 2-amino-3-pyrazine carboxylate ester. 2-phenylamino-3-pyrazine carboxylic acid is a known compound, C.A., 75, 20154e (1971). The esters, III, may be prepared by standard procedures.

When utilized herein and in the appended claims the below listed terms, unless specified otherwise, are defined as follows:

halogen—fluorine, chlorine, bromine and iodine;
alkyl—straight and branched carbon chains containing from 1 to 10 carbon atoms;
hydroxyalkyl and dihydroxyalkyl having from 2 to 6 carbons—hydroxyalkyl and dihydroxyalkyl groups wherein the hydroxy group(s) is not substituted at the position alpha to the oxygen to which the $R_2$ group is attached.
$R_2$ is alkenyl and alkynyl having from 3 to 8 carbon atoms-alkenyl and alkynyl groups wherein the unsaturation is not at the position alpha to the oxygen to which the $R_2$ group is attached.

Pharmaceutically acceptable metal and amine—metals and amines that are generally recognized as being non toxic, such as sodium, potassium, calcium, aluminum, N-methylglucamine, lysine and the like.

The active compounds utilized in the methods of this invention, are substituted 1,8-naphthyridines and substituted 1,5,8-azanaphthyridines and may exist as solvates, for example as hydrates. The compounds are useful for treating chronic obstructive lung diseases such as asthma, bronchitis and the like because they have been shown by standard test procedures to inhibit the release of mediators such as SRS-A (slow reacting substance of anaphylaxis) and histimine and to antagonize the action of SRS-A on respiratory tissue. These chronic obstructive lung diseases can result from allergic reactions or have non-allergic causes. The compounds used in the methods of this invention can thus be used to treat allergy caused diseases and their preferred use is for treating allergic chronic obstructive lung diseases. Chronic obstructive lung diseases as used herein means disease conditions in which the passage of air through the lungs is obstructed or diminished such as in the case in asthma, bronchitis and the like.

The anti-allergy method of this invention is identified by tests which measure a compound's inhibition of anaphylactic bronchospasm in sensitized guinea pigs having antigen induced SRS-A bronchoconstriction. The compounds are orally effective non-adrenergic, non-anticholinergic antianaphylactic agents. When administered orally they are active at dosages of from about 2 to 100 mg/kg of body weight; when administered parenterally, e.g. intravenously, the compounds are active at dosages of from about 1 to 10 mg/kg body weight.

In in vitro tests, the compounds utilized in the methods of this invention antagonize contractions of lung parenchymal strips caused by leukotriene $C_4$. They are found to be active from these and other tests, as well as by comparison with compounds known to be effective for treating chronic obstructive lung diseases such as asthma or bronchitis. In the preferred anti-allergy use, the compounds of this invention are used to treat allergic patients by administering an anti-allergy effective amount thereof. The allergies treated can be, for example, asthma, as well as other chronic obstructive lung diseases.

Certain of the compounds described herein possess gastrointestinal cytoprotectant effects.

The active compounds can be administered orally, topically, parenterally, or by oral or nasal inhalation. The preferred mode of administration is orally.

The amount and frequency of administration will be regulated accordingly to the judgement of the attending clinician considering such factors as age, condition and size of the patient as well as severity of the disease being treated. A typical recommended dosage regimen is oral administration of from 200 to 1500 mg/day, preferably 500 to 800 mg/day, in two to four divided doses to achieve relief of the symptoms.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal or oral spray. Insufflation is also contemplated. Topical dosage forms can be creams, ointments, lotions and the like. Other dosage forms which can be used are transdermal devices.

The following examples illustrate the preparation of the compounds used in the methods of this invention as well as pharmaceutical compositions containing the compounds. All temperatures are in degrees Celsius.

EXAMPLE 1

3-(n-Butyl)-4-hydroxy-1-(3-methylthiophenyl)-1,8-naphthyridin-2(1H)one

To a stirred solution of 11 g. of methyl 2-(3-methylthiophenylamino)-3-pyridine carboxylate in 110 ml. of ethyl caproate there is added, portionwise, 8.96 g. of potassium tertiary butoxide in an atmosphere of nitrogen. The reaction mixture is heated to an internal temperature of 140°–142° for two hours, cooled and the potassium salt is collected by filtration. The crude potassium salt is dissolved in 150 ml of water, acidified with 10% hydrochloric acid and the product filtered and dried; weight 12.1 g., m.p. 245°–246° C. Recrystallization from pyridine-ether gives a colorless solid, m.p. 245°–246° C.

Prepare the 3-(n-butyl)-4-hydroxy-1-phenyl-1,8-naphthyridin-2(1H)one by the process of Example 1 by replacing the methyl 2-(3-methylthiophenylamino)-3-pyridine carboxylate with an equivalent amount of methyl 2-phenylamino-3-pyridine carboxylate.

EXAMPLE 1A

4-Hydroxy-1-phenyl-1,8-naphthyridin-2(1H)-one

To a stirred solution of 1 kg. of methyl 2-phenylamino-3-pyridine carboxylate in 3.97 liters of n-butyl acetate there is added portionwise, 1.1 kg. of potassium tertiary butoxide. After the addition of the potassium tertiary butoxide, there is added an additional 1.32 liters of n-butyl acetate. The reaction mixture is heated to reflux for 20 hours during which the internal temperature of the reaction mixture rose from 90° C. to 122° C. During this period, 1.8 liters of liquid is removed from the reaction mixture via a Dean-Stark trap. Xylene (3.0 liters) is added to the reaction mixture and the remainder of the n-butyl acetate is removed via the Dean-Stark trap. The reaction mixture is cooled and the potassium salt is collected by filtration, washed with toluene and air dried. The crude potassium salt is dissolved in 12 liters of water, the aqueous solution is extracted with toluene, acidified to pH 2 and the product filtered and dried; weight 937 g., m.p. 311°–313° C.

EXAMPLE 2

4-Acetoxy-1-phenyl-3-(2-propenyl)-1,8-naphthyridine-2(1H)-one (A)

4-(2-propenyloxy)-1-phenyl-1,8-naphthyridin-2(1H)-one

To a mixture of 62 g. of 4-hydroxy-1-phenyl-1,8-naphthyridin-2(1H)-one, 39.6 g. of anhydrous potassium carbonate and 1,800 ml of acetone there is added dropwise, with stirring, 37.5 g. of allyl bromide. The reaction mixture is refluxed for 22 hours, concentrated in vacuo, and the residue extracted with 600 ml. of chloroform. The organic extract is washed with water, 1N sodium hydroxide solution and again with water, dried over anhydrous magnesium sulfate, filtered and concentrated. The crude solid is triturated with 3×400 ml of boiling isopropyl ether, filtered, yielding the insoluble product, wt. 38.5 g. m.p. 171°–174°. Recrystallization from methanol produces the product as a colorless solid, m.p. 176°–177° C.

(B)
4-Acetoxy-1-phenyl-3-(2-propenyl)-1,8-naphthyridin-2(1H)-one

A mixture of 33.8 g. of 4-(2-propenyloxy)-1-phenyl-1,8-naphthyridin-2(1H)-one and 35 ml. of acetic anhydride is refluxed for four hours. On cooling, the reaction mixture solidified. Trituration with isopropyl ether and filtration yields the product, 36.1 g., as a colorless solid, m.p. 189°–195° C. Recrystallization from ethanol provides the product of this example melting at 195°–196° C.

EXAMPLE 3

4-Hydroxy-1-phenyl-3-(2-propenyl)-1,8-naphthyridin-2(1H)-one

A mixture of 6.0 g. of 4-acetoxy-1-phenyl-3-(2-propenyl)-1,8-naphthyridin-2(1H)-one, 200 ml. of ethanol and 40 ml. of 1N sodium hydroxide solution is stirred at room temperature for 22 hours. The ethanol is removed in vacuo and the remaining aqueous solution acidified with 1N hydrochloric acid. The product is filtered, washed with water and dried, weight 5.3 g., m.p. 248°–250° C. Recrystallization from chloroform yields the product of this example as a colorless solid, m.p. 250°–252° C.

EXAMPLE 4

7-(n-Butyl)-8-hydroxy-5-phenylpyrido-[2,3-b]pyrazine-6(5H)-one (A) Methyl 2-bromo-3-pyrazine carboxylate To a stirred mixture of 12.7 g. of methyl 2-amino pyrazine 3-carboxylate and 47 ml. of 48% hydrobromic acid there is added, dropwise, 12.6 ml. of bromine keeping the temperature at 0°. A solution of 14.4 g. of sodium nitrite in 60 ml. of water is then added, dropwise, at 0° and the reaction mixture stirred for 15 minutes. The reaction mixture is basified to pH 8 with sodium bicarbonate and extracted with ethyl acetate and again with chloroform. The organic layers are dried over magnesium sulfate, filtered and concentrated to a yellow oil. Recrystallization from ether-hexane yields the product, m.p. 43°–45° C.

(B) Methyl 2-phenylamino-3-pyrazine carboxylate

A mixture of 9.5 g. of methyl 2-bromo-3-pyrazine carboxylate, 8.2 g. of aniline, 0.5 g. of p-toluene sulfonic acid and 100 ml. of water is stirred and refluxed for two hours. The reaction mixture is poured on ice, extracted with ethyl acetate, the organic extracts are dried and concentrated to yield an oil. The crude residue is eluted on a silica gel column with ethylacetate-hexane (1:2) yielding the product of this example as a yellow solid, m.p. 72°–75° C.

(C)
7-(n-Butyl)-8-hydroxy-5-phenyl-pyrido[2,3-b]pyrazine-6(5H)one

A mixture of 3.5 g. of methyl 2-phenylamino-3-pyrazine carboxylate, 30 ml. of ethyl caproate and 4 g. of potassium tertiary butoxide is stirred and heated under nitrogen at 150°–160° for one and a half hours. The reaction mixture is poured on ice, extracted with ethyl acetate and the ethyl acetate extracts washed with water. The combined aqueous layers are acidified to pH 5.5 with dilute hydrochloric acid and the solid filtered. Recrystallization from ethyl acetate-hexane yields the product of this example as a colorless solid; m.p. 183°–185° C.

EXAMPLE 5

3-(2-Hydroxyethyl)-4-hydroxy-1-phenyl-1,8-naphthyridin-2(1H)one

To a solution of 6.8 g. of methyl 2-phenyl-amino-3-pyridine carboxylate in 60 ml. of gamma-butyrolactone there is added, under nitrogen, 13.4 g. of potassium tertiary butoxide. The reaction mixture is heated and stirred for one hour at 95° C., poured on ice and stirred overnite. The mixture is extracted with ether, the aqueous layer acidified with acetic acid to pH 4.5 and the product is collected by filtration. Recrystallization from chloroform, acetone, isopropanol yields the product of this example as a colorless solid; m.p. 235°–236° C.

EXAMPLE 6

4-hydroxy-1-phenyl-3-(2-pyridyl)-1,8-naphthyridin-2(1H)one

To a stirred solution of 5.8 gm of methyl 2-phenylamino-3-pyridine carboxylate and 25 gm of ethyl 2-pyridylacetate there is added, portionwise, 5.7 gm of potassium tertiary butoxide under a nitrogen atmosphere. The system is heated to an internal temperature of 105° C. for 10 minutes. The reaction is cooled to room temperature, diluted with 100 ml of diethyl ether and the brown precipitate collected by filtration. The precipitate is washed with 200 ml water and the filtrate is acidified to pH 3–4 with a 15% HCl solution whereupon the product separates. The precipitate is filtered and dried to give 6.3 gm of crude 4-hydroxy-1-phenyl-3-(2-pyridyl)-1,8-naphthyridin-2(1H)one; recrystallization from pyridine yields the title product; m.p. 332°–333° C.

EXAMPLE 7

3-(n-Butyl)-4-(2-hydroxyethoxy)-1-phenyl-1,8-naphthyridin-2(1H)one

Reflux a stirred solution of 16.2 gm of 3-(n-butyl)-4-hydroxy-1-phenyl-1,8-naphthyridin-2(1H)one and 11.4 gm of anhydrous potassium carbonate powder in 600 ml of dry acetone for 30 minutes. 95% 2-bromoethanol (10.3 gm) is added dropwise to the solution. The reaction is refluxed for 26 hours, cooled and the solvent removed by stripping. The resulting solid is dissolved in 500 ml chloroform and the chloroform solution is washed with 300 ml water, twice with 100 ml of 0.5N sodium hydroxide solution and finally with 100 ml of water. The chloroform solution is dried over magnesium sulfate, filtered and the solvent is removed to give the crude product. The crude product is triturated with warm isopropyl ether to give 10.9 gm of the 3-(n-butyl)-4-(2-hydroxyethoxy)-1-phenyl-1,8-naphthyridin-2(1H)one; which after recrystallization from acetone melts at 138°–140° C.

EXAMPLE 8

3-(n-Butyl)-4-[2-(2-hydroxyethoxy)ethoxy]-1-phenyl-1,8-naphthyridin-2(1H)one

To a mixture of 6.8 g. of 3-(n-Butyl)-4-(2-hydroxyethoxy)-1-phenyl-1,8-naphthyridin-2(1H)one and 150 ml of anhydrous dioxane is added 0.8 g. of sodium hydride (60% oil dispersion) with stirring. The reaction mixture is stirred and warmed on a steam bath for 30 minutes, followed by dropwise addition of 2.6 g. of 95% 2-bromoethanol. The reaction mixture is stirred and refluxed for 24 hours, the solvent is removed in vacuo and the residual solid is dissolved in chloroform. The chloroform solution is successively washed with water, 0.5N sodium hydroxide and water, the organic layer is dried over magnesium sulfate, filtered and concentrated to dryness to yield the product of this example.

The following formulations exemplify some of the dosage forms of the compositions of this invention. In each, the term "active compound" designates a compound of formula I.

PHARMCEUTICAL DOSAGE FORM EXAMPLES

Example A

| No. | Ingredient | Tablets mg/tablets | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixture for 10–15 minutes. Granulate the mixture with Item No. 3. Mill the drop granules through a coarse screen (e.g., ¼″) if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

Example B

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

| Ingredient | Parenteral mg/vial | mg/vial |
|---|---|---|
| Active Compound Sterile Powder | 100 | 500 |

Add sterile water for injection or bacteriostatic water for injection for reconstitution.

Example D

| Ingredient | Injectable mg/vial | mg/vial |
|---|---|---|
| Active Compound | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25°–35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.
6. Terminally sterilize the units by autoclaving.

Example E

| Nasal Spray | mg/ml |
|---|---|
| Active Compound | 10.0 |
| Phenyl Mercuric Acetate | 0.02 |
| Aminoacetic Acid USP | 3.7 |
| Sorbitol Solution | 57.0 |
| Benzalkonium Chloride Solution | 0.2 |
| Sodium Hydroxide 1N Solution to adjust pH | — |
| Water Purified USP to make | 1.0 ml |

I claim:

1. A compound having the structural formula I

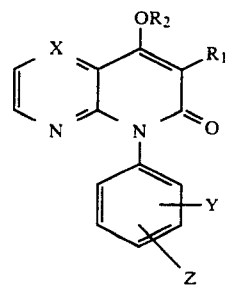

wherein
X is CH;
Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-S(O)$_m$- having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;
Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;

$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, carboxylic acyl having from 3 to 6 carbon atoms or substituted alkyl having from 1 to 10 carbon atoms which is substituted with a substituent selected from hydroxy, halogen, alkoxy having from 1 to 6 carbon atoms, phenyl, carboxylic acyl having from 2 to 6 carbon atoms, cycloalkyl having from 3 to 7 carbon atoms or carboxylic acyloxy having from 1 to 6 carbon atoms;

$R_2$ is hydrogen, carboxylic acyl having from 1 to 6 carbon atoms, alkenyl having from 3 to 8 carbon atoms, alkynyl having from 3 to 8 carbon atoms, $R_a R_b N(CH_2)_n$- (wherein $R_a$ and $R_b$ are hydrogen, alkyl having from 1 to 6 carbon atoms and n is an integer of from 2 to 6) hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine.

2. A compound having the structural formula defined in claim 1 wherein $R_1$ is alkenyl having from 2 to 10 carbon atoms.

3. A compound having the structural formula defined in claim 2 wherein $R_1$ is 2-propenyl.

4. A compound having the structural formula defined in claim 1 wherein $R_1$ is alkynyl having from 2 to 10 carbon atoms.

5. A compound having the structural formula defined in claim 1 wherein $R_1$ is cycloalkyl having from 3 to 8 carbon atoms.

6. A compound having the structural formula defined in claim 1 wherein $R_1$ is alkyl having from 1 to 10 carbon atoms which is substituted with a substituent selected from hydroxy, halogen, alkoxy having from 1 to 6 carbon atoms, phenyl, cycloalkyl having from 3 to 7 carbon atoms or carboxylic acyloxy having from 1 to 6 carbon atoms.

7. A compound having the structural formula defined in claim 6 wherein $R_1$ is 2-hydroxyethyl.

8. A compound having the structural formula defined in claim 6 wherein $R_1$ is 4-propionyloxybutyl.

9. A compound having the structural formula defined in claim 1 wherein $R_2$ is alkynyl having from 3 to 8 carbon atoms.

10. A compound having the structural formula defined in claim 1 wherein $R_2$ is $R_a R_b N(CH_2)_n$- wherein $R_a$ and $R_b$ are hydrogen, alkyl having from 1 to 6 carbon atoms and n is an integer of from 2 to 6.

11. A compound having the structural formula defined in claim 1 wherein $R_2$ is hydroxyalkyl having from 2 to 6 carbon atoms.

12. A compound having the structural formula defined in claim 1 wherein $R_2$ is dihydroxyalkyl having from 2 to 6 carbon atoms.

13. A compound having the structural formula defined in claim 1 wherein $R_2$ is hydroxyalkoxyalkyl having from 2 to 8 carbon atoms.

14. A compound having the structural formula defined in claim 1 wherein $R_2$ is carboxylic acyl having from 2 to 4 carbon atoms.

15. A compound having the structural formula defined in claim 1 wherein $R_2$ is hydrogen or the sodium cation.

16. A compound having the structural formula defined in claim 1 wherein $R_2$ is ethanoyl, —COCH$_3$.

17. A compound having the structural formula defined in claim 1 wherein $R_2$ is propanoyl, —COC$_2$H$_5$ or 2-hydroxyethyl, —CH$_2$CH$_2$OH.

18. A compound having the structural formula defined in claim 1 wherein Z is hydrogen.

19. The compounds defined in claim 18 wherein Y is in the ortho position.

20. The compounds defined in claim 18 wherein Y is in the meta position.

21. The compounds defined in claim 18 wherein Y is in the para position.

22. The compounds having the structural formula defined in claim 1 wherein $R_1$ is omega-hydroxyalkyl having from 2 to 4 carbon atoms.

23. The compounds having the structural formula defined in claim 1 wherein $R_1$ is alkenyl having from 3 to 4 carbon atoms.

24. The compounds having the structural formula defined in claim 1 wherein $R_1$ is propen-2-yl, —CH$_2$CH=CH$_2$.

25. The compounds having the structural formula defined in claim 1 wherein $R_1$ is 3-hydroxypropyl.

26. The compounds having the names:
1-phenyl-4-propionyloxy-3-(4-propionyloxybutyl)-1,8-naphthyridin-2(1H)-one;
4-hydroxy-1-(3-methoxyphenyl)-3-(2-propenyl)-1,8-naphthyridin-2(1H)-one;
4-acetoxy-1-phenyl-3-(2-propenyl)-1,8-naphthyridin-2(1H)-one;
4-hydroxy-3-(3-hydroxypropyl)-1-phenyl-1,8-naphthyridin-2(1H)-one;
4-hydroxy-3-(2-hydroxyethyl)-1-phenyl-1,8-naphthyridin-2(1H)-one; and
4-hydroxy-1-phenyl-3-(2-propenyl)-1,8-naphthyridin-2(1H)-one.

27. The compound having the name 4-acetoxy-1-phenyl-3-(2-propenyl)-1,8-naphthyridin-2(1H)-one.

28. A method for treating allergic reactions in a mammal which method comprises administering an antiallergic effective amount of a compound having the structural formula I

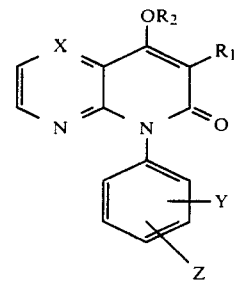

wherein
X is CH;
Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-S(O)$_m$- having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;

Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;

$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, carboxylic acyl having from 2 to 6 carbon atoms or alkyl having from 1 to 10 carbon atoms which may be substituted with hydroxy, halogen, alkoxy having from 1 to 6 carbon atoms, phenyl, carboxylic acyl having from 2 to 6 carbon atoms, cycloalkyl having from 3 to 7 carbon atoms or carboxylic acyloxy having from 1 to 6 carbon atoms;

$R_2$ is hydrogen, carboxylic acyl having from 1 to 6 carbon atoms, alkenyl having from 3 to 8 carbon atoms, alkynyl having from 3 to 8 carbon atoms, $R_a R_b N(CH_2)_n$- (wherein $R_a$ and $R_b$ are hydrogen, alkyl having from 1 to 6 carbon atoms n is an integer of from 2 to 6) hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine;

with the proviso that when X is CH, Y and Z are both hydrogen and $R_1$ is n-butyl; $R_2$ is not hydrogen or a cation derived from a pharmaceutically acceptable metal or an amine with the further proviso that when X is CH, Y and Z are both hydrogen and $R_1$ is n-butyl; $R_2$ is not allyl.

29. The method defined in claim 1 wherein the compound is 4-acetoxy-1-phenyl-3-(2-propenyl)-1,8-naphthyridin-2(1H)-one.

30. The method defined in claim 1 wherein the compound is 3-(n-butyl)-4-(2-hydroxyethoxy)-1-phenyl-1,8-naphthyridin-2(1H)-one.

31. The method defined in claim 1 wherein the compound is 4-hydroxy-3-(3-hydroxypropyl)-1-phenyl-1,8-naphthyridin-2(1H)-one.

32. The method defined in claim 1 wherein the compound is 4-hydroxy-1-(3-methoxyphenyl)-3-(2-propenyl)-1,8-naphthyridin-2(1H)-one.

33. The method defined in claim 1 wherein the compound is 1-phenyl-4-propionyloxy-3-(4-propionyloxybutyl)-1,8-naphthyridin-2(1H)-one.

34. The method defined in claim 1 wherein the compound is 4-hydroxy-3-(2-hydroxyethyl)-1-phenyl-1,8-naphthyridin-2(1H)-one.

35. The method defined in claim 1 wherein the compound is 3-(n-butyl)-4-hydroxy-1-(3-methylthiophenyl)-1,8-naphthyridin-2(1H)-one.

36. The method defined in claim 1 wherein $R_1$ is n-alkyl having from 3 to 5 carbon atoms.

37. The method defined in claim 1 wherein $R_1$ is alkenyl having from 3 to 4 carbon atoms.

38. The method defined in claim 1 wherein $R_1$ is propen-2-yl, $-CH_2CH=CH_2$.

39. The method defined in claim 1 wherein $R_1$ is 3-hydroxypropyl.

40. The method defined in claim 1 wherein $R_2$ is hydrogen or the sodium cation.

41. The method defined in claim 1 wherein $R_2$ is carboxylic acyl having from 2 to 4 carbon atoms.

42. The method defined in claim 1 wherein $R_2$ is ethanoyl, $-COCH_3$.

43. The method defined in claim 1 wherein $R_2$ is propanoyl, $-COC_2H_5$ or 2-hydroxyethyl, $-CH_2CH_2OH$.

44. The method defined in claim 1 wherein Z is hydrogen.

45. The method defined in claim 44 wherein Y is in the ortho position.

46. The method defined in claim 44 wherein Y is in the meta position.

47. The method defined in claim 44 wherein Y is in the para position.

* * * * *